United States Patent [19]
Meingassner et al.

[11] Patent Number: 5,985,906
[45] Date of Patent: Nov. 16, 1999

[54] ANTIFUNGAL COMPOSITION

[75] Inventors: Josef Gottfried Meingassner, Perchtoldsdorf; Neil Stewart Ryder, Vienna, both of Austria

[73] Assignee: Novartis AG, Basel, Switzerland

[21] Appl. No.: 08/952,288

[22] PCT Filed: May 10, 1996

[86] PCT No.: PCT/EP96/02022

§ 371 Date: Nov. 12, 1997

§ 102(e) Date: Nov. 12, 1997

[87] PCT Pub. No.: WO96/35423

PCT Pub. Date: Nov. 14, 1996

[30] Foreign Application Priority Data

May 12, 1995 [GB] United Kingdom ............... 9509631

[51] Int. Cl.$^6$ ...................... A61K 31/41; A61K 31/135; A01N 43/64; A01N 33/02

[52] U.S. Cl. ...................... 514/383; 514/650; 514/655; 514/657

[58] Field of Search ............................. 514/650, 655, 514/657, 383

[56] References Cited

U.S. PATENT DOCUMENTS

| | | | |
|---|---|---|---|
| 5,214,046 | 5/1993 | Guerry et al. | 514/255 |
| 5,696,164 | 12/1997 | Sun et al. | 514/562 |

FOREIGN PATENT DOCUMENTS

| | | |
|---|---|---|
| 0006711 | 1/1980 | European Pat. Off. . |
| 0401798 | 12/1990 | European Pat. Off. . |
| 0410359 | 1/1991 | European Pat. Off. . |
| 0310122 | 7/1991 | European Pat. Off. . |
| 0464465 | 1/1992 | European Pat. Off. . |
| 2804096 | 8/1978 | Germany . |
| 3038521 | 7/1989 | Japan . |
| 3038522 | 7/1989 | Japan . |
| 2099818 | 12/1982 | United Kingdom . |
| 2197194 | 5/1988 | United Kingdom . |

OTHER PUBLICATIONS

"Recent Advances with the Allylamine Antimycotic Terbinafine", Lecture at 1995 Antifungal Drug Discovery Summit, Princeton, NJ, Oct. 30–31, 1995.
A. Polak, "Combination of Amorolfine with Various Antifungal Drugs in Dermatophytosis," Mycoses, vol. 36, 1993, pp. 43–49.
A. Polak-Wyss, "Mechanism of Action of Antifungals and Combination Therapy," Journal of the European Academy of Dermatology and Venereology, vol. 4, (Suppl. 1), 1995, pp. S11–S16 (+ Abstract).
Abstract of Ann. Meeting Am. Soc. Microbiol. 87 (1987) 392 (Enclosure 7), disclosing synergy in vivo of combination ketoconazole–terbinafine.
Ando et al., "Synerazol, A New Antifungal Antibiotic," The Journal of Antibiotics, vol. 44, 1991, pp. 382–389 (+ Abstract).
Barret–Bee et al., "Ergosterol Biosynthesis Inhibition: a Target for Antifungal Agents," Acta Biochimica Polonica, vol. 42, NO. 4, 1995, pp. 465–480 (+ Abstract).
Barrett–Bee et al, "Biochemical Aspects of Ergosterol Biosynthesis Inhibition," Emerging Targets for Antibacterial and Antifungal Chemotherapy, Chapt. 16, 1992. pp. 410–436.
Bossche et al., "Characterization of an Azole–Resistance Candida Glabrata Isolate," Antimicrobial Agents and Chemotherapy, vol. 36, No. 12, 1992, pp. 2602–2610.
D. Kerridge, "Antifungal Drugs," Drugs Today, vol. 24, 1988, pp. 705–715.
Drouhet et al., "Evolution of Antifungal Agents: Past, Present, and Future," Reviews of Infectious Diseases, vol. 9, Supplement 1, 1987, pp. S4–S14 (+ Abstract).
Guy St.–Germain, "Effects of Pentamidine Alone and in Combination with Ketoconazole or Itraconazole on the Growth of Candida Albicans," Anitmicrobial Agents and Chemotherapy, vol. 34, No. 12, 1990, pp. 2304–2306.
Hiratani et al., "Cross–Resistance of Candida Albicans to Several Different Ergosterol Synthesis Inhibitors," Jap. J. Antibiotics, vol. 47, No. 2, 1994, pp. 125–128 (+ Abstract).
J. Perfect, "Antifungal Therapy," Curr. Opin. Infect. Dis., vol. 1, No. 4, 1988, pp. 590–594.
Maldonado et al., "Experimental Chemotherapy with Combinations of Erogostrol Biosysthesis Inhibitors in Murine Models of Chagas' Disease," Antimicrobial Agents and Chemotherapy, vol. 37, No. 6, 1993, pp. 1353–1359 (+ Abstract).
Mikami et al., "Comparison of Antifungal Activity of Amphotericin B. Miconazole, Itraconazole, Flucytosine, and Fluconazole Against Clinically Isolated Cryptococcus Neoformans by MIC and IC50 Values, and Their Combination Effects," Chemotherapy, vol. 39, (+ Abstract), 1991.
Paul D. Hoeprich, "Antifungal Chemotherapy," Progress in Drug Research, vol. 44, 1995, pp. 87–127.
Polak et al., "Anifungal Chemotherapy—Are We Winning?", Fortschr. Arzneimittelforsch., vol. 37, 1991, pp. 181–269 (+ Abstract).
Rinaldi et al., "Combination Antifungal Susceptibility Testing of Terbinafine and the Triazoles Fluconazole and Itraconazole," Interscience Conference on Antimicrobial Agents and Chemotherapy, San Francisco, Sep. 17–20, 1995.
Sud et al., "Effect of Ketoconazole in Combination with Other Inhibitors of Sterol Synthesis on Fungal Growth," Antimicro. Agents Chemother., vol. 28, (1985), pp. 532–534 (+ Abstract).
Urbina et al., "Antiproliferative Synergism of the Allylamine SF 86–327 and Ketoconazole on Epimastigotes and Amstigotes of Trypanosoma (Schizotrypanum) cruzi," Antimicrob. Agents Chemother., vol. 32, 1988, pp. 1237–1242 (+ Abstract).
Uno et al., Chemical Abstracts 115:142274 (1991), copy of abstract.

*Primary Examiner*—Kevin E. Weddington
*Attorney, Agent, or Firm*—Carol A. Loeschorn

[57] ABSTRACT

Use of a combination of the squalene epoxidase inhibitor terbinafine and an azole 14-alpha-methyldemethylase inhibitor (fluconazole or itraconazole) in mycotic infections caused by azole-resistant fungal strains, and corresponding pharmaceutical compositions, process and method.

20 Claims, No Drawings

ANTIFUNGAL COMPOSITION

This is a 371 of PCT/EP96/02022, filed May 10, 1996.

The present invention relates to the treatment of human mycotic infections. It concerns antifungal compositions for use in the treatment of mycotic infections caused by azole resistant yeast strains, comprising terbinafine with an azole 14α-methyldemethylase inhibitor such as the azole fluconazole and/or itraconazole.

Although they are often present as benign commensal organisms in the digestive tract of healthy individuals, fungi, particularly Candida species produce a broad range of serious illnesses in compromised hosts. Such infections are clearly on the rise. Oropharyngeal candidiasis is the most common fungal infection in patients with human immunodeficiency virus (HIV) infection. With the introduction of azole antifungal agents that are bioavailable after oral administration, the approach to the treatment of serious Candida infections is possible. Ketoconazole, the first of there agents to become available, was quickly found to be efficacious in the setting of chronic mucocutaneous candidiasis. However, not long after the introduction of this agent, clinical failure in association with elevated minimum inhibitory concentrations (MICs) of ketoconazole that developed during prolonged therapy were reported. This problem achieved prominence with the subsequent introduction of fluconazole. Fluconazole, a water-soluble triazole with greater than 90% bioavailability after oral administration, is used extensively to treat a wide range of Candida infections. In particular, it is widely used as therapy for oropharyngeal candidiasis in patients with advanced HIV infection and AIDS. Although oropharyngeal candidiasis usually responds readily to fluconazole, it is difficult to completely eradicate the infection and relapse often occurs within several months following the completion of therapy. For this reason, many AIDS patients receive fluconazole either continuously on intermittently over long periods of time.

To a greater extent than with other azoles, resistance to fluconazole has developed and is becoming a significant clinical problem, as attested by isolation from, in particular, AIDS patients of numerous Candida strains showing resistance (see e.g. D. Law et al., *J. Antimicrob. Chemother.* 34 [1994] 659–668).

It has now been found that, surprisingly, a combination of the squalene epoxidase inhibitor terbinafine (Lamisil®) and an azole 14α-methyldemethylase inhibitor such as fluconazole and/or itraconazole is active against azole-resistant fungal strains. By using this combination of compounds there is provided a method for treating human mycotic infections caused by azole-resistant fungal strains.

Suitable azole 14α-methyldemethylase inhibitors are in particular imidazole and triazole antifungal agents.

Preferred imidazole antifungal agents include clotrimazole (*Arzneim.-Forsch.* 22 [1972] 1280), miconazole (*Arzneim.-Forsch.* 21 [1971] 256; econazole (*Arzneim.-Forsch.* 25 [1975] 224); isoconazole (*Arzneim.-Forsch.* 29 [1979] 1344); trioconazole (*Antimicrobial Agents Chemotherapy* 15 [1979] 597–602); sulconazole (*Eumycetes and Mycosis* 23 [1982] 314–317; oxiconazole (*Arzneim.-Forsch.* 32 [1982] 17–24); cloconazole (*J. Med. Chem.* 26 [1983] 768–770); bifonazole (*Arzneim.-Forsch.* 33 [1983] 517–524); butoconazole (*J. Med. Chem.* 21 [1978] 840; fenticonazole (*Arzneim.-Forsch.* 31 [1981] 2127); zinoconazole (*J. Med. Chem.* 26 [1983] 442–445) and ketoconazole (*J. Med. Chem.* 22 [1979] 1003–1005).

Preferred triazole antifungal agents include terconazole (*J. Med. Chem.* 26 [1983] 611–613); itraconazole (*Antimicrobial Agents and Chemotherapy* 26 [1984] 5–9); vibunazole (*Arzneim.-Forsch.* 33 [1983] 546); fluconazole (*Antimicrobial Agents and Chemotherapy* 27 [1985] 815–818), and (R)(-)-α-(4-chlorophenyl)-α-(1-cyclopropyl-1-methylethyl)-1H-1,2,4-triazol-1-ethanol in free form or in salt or metal complex form (GB 2'161'483) (hereinafter briefly referred to, in free form, as "compound A").

Especially preferred azoles are itraconazole and fluconazole.

Not all combinations of antifungal drugs show synergistic or even additive effects, and even antagonistic effects have been reported in the literature. Thus in e.g. E. Martin et al., *Antimicr. Agents and Chemother.* 38 [1994] 1331–1338, it has been reported that fluconazole antagonizes the candidacidal action of amphotericin B; in *Abstr. Ann. Meeting Am. Soc. Microbiol.* 87 (1987) 392 it was reported that the use of terbinafine and ketoconazole in *Candida albicans* produced no enhancement of antimycotic activity; in *Eur. J. Clin. Microbiol. Infect. Dis.* 7 (1988) 732–735 it was stated that in vitro terbinafine appears to act antagonistically with the azoles; and in *Drugs Today* 24 (1988) 705–715 it is again mentioned that in combination therapy, not all combinations of antifungal drugs show synergistic or even additive effects.

It appears therefore that combination therapy with antimycotics is highly unpredictable.

Thus, while one might on theoretical grounds expect that combinations of pharmacologically active agents that inhibit a single biosynthetic pathway at two separate steps are normally more active than those which act only on one step, and that combinations of e.g. terbinafine with azoles such as fluconazole and/or itraconazole should possess at least additive activity, it is very surprising that, for unknown reasons, such combinations are still effective even where resistance to the azoles has already developed, namely, synergistic effects are maintained even in situations where the mycotic strains have become resistant to the azoles.

The composition of the invention for treating human mycotic infections caused by azole-resistant fungal strains comprises an azole 14α-methyldemethylase inhibitor such as fluconazole and/or itraconazole, and the arylmethylamine squalene epoxidase inhibitor terbinafine of formula

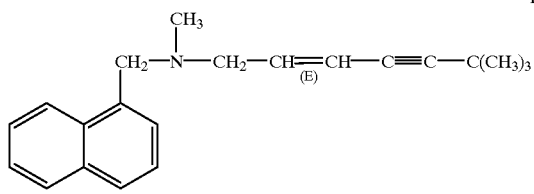

in free base or acid addition salt, e.g. hydrochloride acid addition salt form.

The most preferred azole is fluconazole. Terbinafine preferably is in pharmaceutically acceptable, preferably in hydrochloride salt form. The preferred fungus preferably is a yeast, if preferably is of the genus Candida, it especially is *Candida albicans*. The azole-resistance induced mycosis may be superficial or systemic, it especially is oropharyngeal. It is deleterious to e.g. the skin or mucosa.

The azole-resistance may be a cross-resistance and involve multiple azoles.

The antifungal composition of the present invention is prepared by incorporating the arylmethylamine of formula I to an azole 14α-methyldemethylase inhibiting antifungal agent, such as fluconazole and/or itraconazole.

The invention thus concerns an antifungal composition for use in the treatment of mycotic infections caused by azole-resistant fungal strains for the avoidance or restriction of deleterious azole-resistance induced mycosis, comprising terbinafine as defined above and an azole 14α-methyldemethylase inhibitor, such as fluconazole and/or itraconazole.

It further concerns the use of an antifungal composition comprising terbinafine as defined above and an azole 14α-methyldemethylase inhibitor, such as fluconazole and/or itraconazole, in the preparation of a medicament for use in the treatment of mycotic infections caused by azole-resistant fungal strains for the avoidance or restriction of deleterious azole-resistance induced mycosis in a human subject compromised by such azole-resistance.

It further concerns a process for the preparation of an antifungal composition as defined above, comprising the incorporation of terbinafine as defined above to an azole 14α-methyldemethylase inhibiting antifungal agent, such as fluconazole and/or itraconazole.

It further concerns a method of treatment of an azole-resistant fungal infection caused by azole-resistant fungal strains for the avoidance or restriction of deleterious azole-resistance induced mycosis, comprising administering a therapeutically effective amount of an antifungal composition as defined above to a patient in need of such treatment.

In the antifungal composition of the present invention the weight ratio of the azole antifungal agent to the arylmethylamine antifungal agent may be varied within a wide range, but is preferably within a range of from 100:1 to 1:500, more preferably from 25:1 to 1:125. By mixing the azole antifungal agent and the arylmethylamine antifungal agent terbinafine in a weight ratio within the above range, an excellent effect is obtainable in the treatment of mycosis caused by azole resistant fungal strains, particularly yeast strains, e.g. Candida strains such as *Candida albicans, Candida* (=Torulopsis) *glabrata, Candida krusei* and *Candida tropicalis*; Cryptococcus strains such as *Cryptococcus neoformans*; or Trichophyton strains, e.g. *Trichophyton mentagrophytes*; especially Candida strains, particularly *Candida albicans*.

The composition of the present invention can be adapted for local administration and can be incorporated in a usual pharmaceutical carrier in a wide range of concentrations (usually in an amount of from about 0.1% to about 10% by weight of the total composition) to prepare a formulation. The composition of the present invention can be used for oral administration in the form of tablets, capsules or a liquid, and it may also be used for non-oral administration such as subcutaneous, intramuscular or intravenous injection. It thus normally is a fixed combination. However, administration of the active agents may also be effected in the form of a free combination, i.e. separately, e.g. sequentially, in any order.

The beneficial activity can be shown in vitro using various azole-resistant strains. The assay is performed with RPMI 1640 medium in 96-well, flat-bottom microdilution plates using a chequered drug dilution system. Terbinafine (in hydrochloride salt form) and the azole are used in concentrations from 100 μg/ml to 0.006 μg/ml. Minimal inhibitory concentrations (MIC) are determined after a 48-hour incubation at 37° C. Minimal fungicidal (MFC) concentrations are evaluated 24 hours after transfer of drug-treated cells to drug-free medium. The endpoints used for MIC determination are either 100% inhibition (Tables 1 and 4) or (as is usual) 80% inhibition (Tables 2 and 3) (Terb=terbinafine; Flu=fluconazole; Itra=itraconazole; C.=Candida).

TABLE 1

In vitro testing of the combination terbinafine/fluconazole against fluconazole-resistant strains of *Candida albicans, C. glabrata, C. krusei* and *C. tropicalis*.

| | MIC for 100 % inhibition (μg/ml) | | | |
|---|---|---|---|---|
| | Alone | | Combination | |
| Strain | Terb | Flu | Terb | Flu |
| C. albicans | >100 | >100 | 12.5 | 6.25 |
| C. albicans | >100 | >100 | 12.5 | 12.5 |
| C. albicans | >100 | >100 | 12.5 | 6.25 |
| C. albicans | >100 | >100 | 3.13 | 12.5 |
| C. tropicalis | >100 | >100 | >100 | >100 |
| C. glabrata | >100 | >100 | 3.13 | 25.0 |
| C. albicans | >100 | >100 | 3.13 | 50.0 |
| C. krusei | >100 | 50.0 | 3.13 | 50.0 |

In contrast to exposure of fungi to fluconazole or terbinafine alone, fungal growth was 100% inhibited in all but one strain when combinations of fluconazole and terbinafine were used. In four of the strains, combinations of both drugs at concentrations <100 μg/ml were fungicidal in action, a result which could not be achieved with either of the drugs alone.

TABLE 2

In vitro testing of the combination terbinafine/fluconazole against fluconazole-resistant Candida isolates

| | MIC for 80% inhibition (μg/ml) | | | |
|---|---|---|---|---|
| | Alone | | Combination | |
| Strain | Flu | Terb | Flu | Terb |
| C. albicans | >16 | >1 | 0.25 | 0.1 |
| C. albicans | >16 | >1 | 16 | 0.5 |
| C. tropicalis | >16 | >1 | >0.125 | 0.06 |
| C. glabrata | >16 | >1 | 16 | 0.125 |

TABLE 3

In vitro testing of the combination terbinafine/itraconazole against itraconazole-resistant Candida isolates

| | MIC for 80% inhibition (μg/ml) | | | |
|---|---|---|---|---|
| | Alone | | Combination | |
| Strain | Itra | Terb | Itra | Terb |
| C. albicans | >4 | >1 | ≦0.03 | 0.03 |
| C. tropicalis | >4 | ≦0.03 | >1 | 0.03 |

TABLE 4

In vitro testing af the combination terbinafine/compound A against fluconazole-resistant Candida isalates

| | MIC for 100 % inhibition (μg/ml) | | | |
|---|---|---|---|---|
| | Alone | | Combination | |
| Strain | Compound A | Terb | Compound A | Terb |
| C. albicans | >100 | >100 | 0.4 | 3.13 |
| C. albicans | 100 | >100 | 0.4 | 3.13 |

TABLE 4-continued

In vitro testing af the combination
terbinafine/compound A against fluconazole-resistant Candida isalates

| | MIC for 100 % inhibition (μg/ml) | | | |
|---|---|---|---|---|
| | Alone | | Combination | |
| Strain | Compound A | Terb | Compound A | Terb |
| C. aibicans | 100 | >100 | 1.56 | 3.13 |
| C. albicans | 100 | >100 | 0.8 | 3.13 |

TABLE 5

Summary of azole-resistant fungal strains in which a
combination of terbinafine and an azole was found active and
the azole to which resistance occurred

| Fungal species | Azole | Proportion of strains showing activity |
|---|---|---|
| C. albicans | Fluconazole | 5 of 10 |
| C. albicans | Itraconazole | 9 of 10 |
| C. tropicalis | Fluconazole | 2 of 2 |
| C. krusei | Fluconazole | 1 of 4 |
| C. paratropicalis | Fluconazole | 1 of 1 |
| C. glabrata | Fluconazole | 1 of 2 |
| Cryptococcus neoformans | Fluconazole | 3 of 10 |
| C.albicans | Compound A | 4 of 4 |

We claim:

1. A method of treatment of an azole-resistant fungal infection caused by azole-resistant fungal strains, comprising administering a therapeutically effective amount of terbinafine of formula I

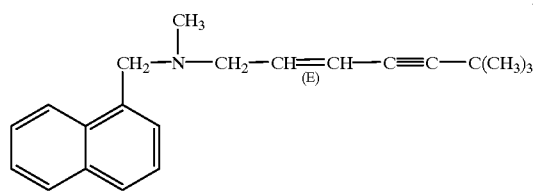

in free base or acid addition salt form, and an azole 14α-methyldemethylase inhibitor, to a patient in need of such treatment.

2. A method according to claim 1 wherein terbinafine is in the form of a hydrochloride salt.

3. A method according to claim 1 wherein the azole is fluconazole.

4. A method according to claim 1 wherein the azole is itraconazole.

5. A method according to claim 1 wherein the azole is (R)-(−)-α-(4-chlorophenyl)-α-(1-cyclopropyl-1-methylethyl)-1H-1,2,4-triazol-1-ethanol in free form or in salt or metal complex form.

6. A method according to claim 1 wherein the azole-resistant fungal strain is a yeast strain.

7. A method according to claim 1 wherein the azole-resistant fungal strain is a Candida strain.

8. A method according to claim 1 wherein the azole resistant fungal strain is Candida albicans.

9. A method according claim 1 wherein the azole-resistant fungal strain is a Cryptococcus strain.

10. A method according to claim 1 wherein the terbinafine and azole are administered together.

11. A method according to claim 1 wherein the terbinafine and azole are administered separately.

12. A method of preventing azole resistance to a fungal infection susceptible to acquiring azole-resistance comprising administering a therapeutically effective amount of terbinafine of formula I

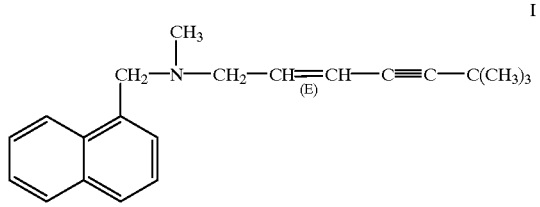

in free base or acid addition salt form, and an azole 14α-methyldemethylase inhibitor, to a patient having a fungal infection susceptible to acquiring azole-resistance.

13. A method according to claim 12 wherein terbinafine is in the form of a hydrochloride salt.

14. A method according to claim 12 wherein the azole is fluconazole.

15. A method according to claim 12 wherein the azole is itraconazole.

16. A method according to claim 12 wherein the azole is (R)-(−)-α-(4-chlorophenyl)-α-(1-cyclopropyl-1-methylethyl)-1H-1,2,4-triazol-1-ethanol in free form or in salt or metal complex form.

17. A method according to claim 12 wherein the fungal infection is caused by a fungal strain susceptible to acquiring azole resistance.

18. A method according to claim 12 wherein the fungal strain is a yeast strain.

19. A method according to claim 12 wherein the terbinafine and azole are administered together.

20. A method according to claim 12 wherein the terbinafine and azole are administered separately.

* * * * *

UNITED STATES PATENT AND TRADEMARK OFFICE
CERTIFICATE OF CORRECTION

PATENT NO : 5,985,906
DATED: : November 16, 1999
INVENTOR(S) : MEINGASSNER ET AL.

It is certified that there is an error in the above-identified patent and that said Letters Patent is hereby corrected as shown below:

Under column 6, claim 18, should read:

-- 18. A method according to claim 17 wherein the fungal strain is a yeast strain. --

Signed and Sealed this

Twelfth Day of December, 2000

Attest:

Q. TODD DICKINSON

*Attesting Officer*     *Director of Patents and Trademarks*